United States Patent [19]

Jackson et al.

[11] Patent Number: 4,980,153
[45] Date of Patent: Dec. 25, 1990

[54] ANTIPLAQUE ORAL HYGIENE COMPOSITION

[75] Inventors: Robert J. Jackson, Weybridge; Nicholas A. Berrill, Wonersh; Shawn V. Robbins, Ottershaw, all of England

[73] Assignee: Beecham Group p.l.c., England

[21] Appl. No.: 324,207

[22] Filed: Mar. 15, 1989

Related U.S. Application Data

[63] Continuation of Ser. No. 65,362, Jun. 23, 1987, abandoned.

[30] Foreign Application Priority Data

Jun. 25, 1986 [GB] United Kingdom ................ 8615534

[51] Int. Cl.$^5$ ............................ A61K 7/18; A61K 7/16
[52] U.S. Cl. ........................................ 424/52; 424/49; 424/50; 424/53; 424/57; 514/900; 514/901; 514/902
[58] Field of Search ................... 424/52, 57, 49, 50, 424/53; 514/900–902

[56] References Cited

U.S. PATENT DOCUMENTS

| | | | |
|---|---|---|---|
| 3,671,644 | 6/1972 | Irani | 424/346 |
| 4,022,880 | 5/1977 | Vinson | 424/54 |
| 4,515,772 | 5/1985 | Parran, Jr. | 424/57 |

FOREIGN PATENT DOCUMENTS

| | | |
|---|---|---|
| 0161898 | 11/1985 | European Pat. Off. . |
| 0161899 | 11/1985 | European Pat. Off. . |
| 1244809 | 9/1971 | United Kingdom . |
| 1526379 | 9/1978 | United Kingdom . |
| 2200551A | 8/1988 | United Kingdom . |

Primary Examiner—F. T. Moezie
Attorney, Agent, or Firm—Jacobs & Jacobs

[57] ABSTRACT

An oral hygiene composition in the form of a dentifrice or a mouthwash, comprising: (a) from 0.01 to 2% by weight of the composition of an antibacterial compound of formula (I):

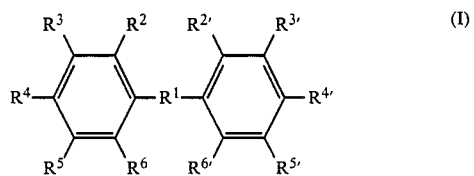

in which $R^1$ is oxygen, sulphur or an alkylene group of from 1 to 6 carbon atoms, each of $R_2$ to $R_6$ and $R^{2'}$ to $R^{6'}$ is hydrogen, hydroxyl or halogen; (b) from 0 to 90% by weight of a dentally acceptable abrasive, (c) from 0.1% to 15% by weight of a dialkali or tetra-alkali metal pyrophosphate salt or a mixture thereof and (d) water.

11 Claims, No Drawings

ANTIPLAQUE ORAL HYGIENE COMPOSITION

CROSS-REFERENCE

This is a continuation of Ser. No. 065,362 filed June 23, 1987, now abandoned.

The present invention relates to an oral hygiene composition containing an antibacterial agent, the function of which is to retard the accumulation of dental plaque and hence reduce the occurrence of caries, calculus and periodontal disease.

Dental plaque forms as a thin film on the surface of teeth, being composed of an aggregation of bacteria and a surrounding matrix. Subsequent mineralisation of the plaque on the enamel surface leads to the formation of calculus. Plaque is now considered to be the prime etiological factor in the development of caries, and it is also implicated in periodontal disease. There is also an association between the presence of calculus and the incidence of periodontal disease (see Harry's Cosmeticology, 7th edition, ed. J. B. Wilkinson and R. J. Moore, George Goodwin 1982, pp 590–592).

Thus, the addition to an oral hygiene composition of an appropriate antibacterial agent, to limit bacterial activity within the oral cavity and hence reduce the growth of plaque, should help to suppress the incidence of caries, calculus and periodontal disease.

U.S. Pat. No. 4,022,880 discloses the use of halogenated bis-phenols and halogenated diphenyl ethers as antibacterial agents in oral hygiene compositions.

A problem associated with the use of such antibacterial agents is that, due to their lipophilic nature, they tend to partition into a hydrophobic oil phase and a surfactant micellar phase and are thereby rendered unavailable for adsorption onto the oral surfaces.

It has now been found that by incorporating certain levels of soluble, alkali metal pyrophosphates into the aqueous oral hygiene formulations, the adsorption of the anti-bacterial agent can be enhanced.

According to the present invention there is provided an oral hygiene composition comprising:

(a) From 0.01 to 2% by weight of the composition of an antibacterial compound of formula (I):

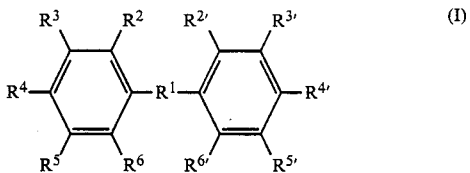

in which $R^1$ is oxygen, sulphur or an alkylene group of from 1 to 6 carbon atoms, and each of $R^2$ to $R^6$ and $R^{2'}$ to $R^{6'}$ is hydrogen, hydroxyl or halogen;

(b) from 0 to 90% by weight of a dentally acceptable abrasive;

(c) from 0.1% to 15% by weight of a dialkali or tetraalkali metal pyrophosphates salt or a mixture thereof, and (d) water.

The preferred weight range of compound (a) is from 0.01 to 1.0%, more preferably 0.05 to 0.5%, the preferred weight range of compound (b) is from 20 to 75%, and that of (c) is from 2 to 10%.

Water should preferably be present in an amount of from 2% to 95%, more preferably from 5% to 50%.

The composition may be in the form of a dentifrice or mouthwash, preferably a dentifrice.

Examples of compounds of formula (I) are:
5,5'-dichloro-2,2'-dihydroxydiphenyl methane; (Dichlorophene).
2,2'-dihydroxy-3,5,6,3',5',6'-hexachloro diphenylmethane; (Hexachlorophene).
3,3'-dibromo-5,5'-dichloro-2,2'-dihydroxydiphenylmethane (Bromochlorophene); and
2,4,4'-trichloro-2'-hydroxydiphenyl ether (Triclosan).

Triclosan is a particularly preferred compound of formula (I).

Examples of dentally acceptable abrasives are insoluble calcium salts such as calcium carbonate, dicalcium phosphate and calcium pyrophosphate; and also alumina; silica and synthetic plastics resin particles.

The silica abrasive can be a precipitated silica or a silica gel, such as the silica gels described in U.S. Pat. No. 3,538,230. Preferred silica gels are marketed under the trade name 'Syloid' by W. R. Grace and Company, Davison Chemicals Division. Preferred precipitated silicas are those marketed under the trade name 'Zeident' by the J. M. Huber Corporation. The pyrophosphate component (c) should have a high degree of available pyrophosphate anions, and accordingly the preferred abrasives are non-calcium based materials such as silica or alumina so as to avoid the formation of insoluble calcium pyrophsate. Calcium pyrophosphate itself, however, can be used as the abrasive since this will not lead to such difficulties. Other insoluble calcium salts can be used provided the formation of free calcium ions is suppressed, and this may be carried out using the method disclosed in U.S. Pat. No. 4,565,691.

Thus, when the abrasive is calcium carbonate, a soluble carbonate such as sodium carbonate is included in the composition. Similarly when the abrasive is calcium phosphate, a sodium phosphate may be included.

The pyrophosphate component (c) may be selected from the following compounds, in hydrated or unhydrated forms:
$Na_4P_2O_7$, $K_4P_2O_7$, $Na_2K_2P_2O_7$, $Na_2H_2P_2O_7$, $K_2H_2P_2O_7$.

Mixtures of any two or more of these materials may be used, the upper percentage limit of each component being dictated largely by solubility and taste considerations.

Ionic fluoride-providing compounds may also be present in the composition of the invention, and these may include ionic fluorides, such as alkali-metal fluorides, preferably sodium fluoride, and/or ionic monofluorophosphates. A preferred ionic monofluorophosphate is an alkali-metal monofluorophosphate, especially sodium monofluorophosphate.

When the composition contains sodium fluoride and a calcium containing abrasive, the formation of free calcium cations can be suppressed, using the method disclosed in EP-A-No. 0 092 929 (U.S. Pat. No. 4,565,691).

The compositions of the invention may optionally contain other agents known to enhance the anti-caries effect of monofluorophosphate, such as calcium glycerophosphate; this being incorporated in a weight ratio of up to 1:3, preferably 1:20 to 1:3, compared to the total weight of monofluorophosphate salt.

Compositions of the present invention may be produced by admixture of the various ingredients.

The compositions of the invention will also usually contain surfactants, gelling agents and other excipients such as flavouring and colouring agents.

The surfactant is normally a water-soluble non-soap or synthetic organic detergent. Suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated mono-aminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Conventional non-ionic surfactants may also be included, if desired.

The surface-active materials are generally present in an amount of 0.05 to 15%, preferably 0.5 to 15%, more preferably 0.5 to 5% by weight of the composition.

In general liquid components in the compositions will comprise chiefly water, glycerine, sorbitol and/or a glycol, including suitable mixtures thereof. Suitably, the glycol is propylene glycol or a polyethylene glycol. It is preferred to use also a gelling agent in dental creams, such as natural or synthetic gums or gumlike materials, e.g. Irish Moss, gum tragacanth, guar gum, sodium carboxymethylcellulose, hydroxyethylcellulose, polyvinyl pyrrolidone, starch or thickening silica. The gelling agent content is usually up to 10% and preferably 0.01 to 5% by weight of the preparation.

Other materials may be added, such as sweetening agents, for example soluble saccharin, flavouring oils such as oils of spearmint, wintergreen, peppermint, chloroform, colouring or whitening agents such as titanium dioxide, preservative such as sodium benzoate, emulsifying agents, silicones, alcohol, menthol, chlorophyll containing compounds, for example, sodium copper chlorophyllin and agents for sensitive dentine, for example strontium salts, formaldehyde.

The compositions of the invention may also be in a form of other oral hygiene compositions, for example, the ingredients may be incorporated in mouthwashes of the suspension type, or in compositions which will be chewed by the user, for example, chewing gum, tablets, pastilles and lozenges. These compositions will contain the conventional base materials together with suitable flavours and sweetening agents and may be formulated in known manner.

Compositions according to the invention are able to reduce plaque growth, thereby having an anti-caries effect. The data in the test section show that the inclusion of a pyrophosphate salt, such as sodium pyrophosphate, to a mouthwash comprising the antibacterial agent triclosan, results in a significant reduction in the growth of dental plaque, over and above that achieved using a mouthwash comprising triclosan alone.

The compositions of the invention are illustrated by the following examples; in which Examples 1 to 5 are dentifrices, Example 6 is a mouthwash, and Example 7 is Test Data.

|  | Example 1 % | Example 2 % | Example 3 % |
|---|---|---|---|
| Glycerine | 24.00 | 24.00 | 24.00 |
| Saccharin (15% soln) | 2.00 | 2.00 | 2.00 |
| Guar gum | 1.00 | 1.00 | 1.00 |
| Titanium dioxide | 1.00 | 1.00 | 1.00 |
| Sodium fluoride | 0.00 | 0.00 | 0.22 |
| Sodium monofluorophosphate | 0.80 | 0.80 | — |
| Preservative | 0.10 | 0.10 | 0.10 |
| Thickening silica | 6.00 | 6.00 | 6.00 |
| Abrasive silica | 14.00 | 14.00 | 14.00 |
| Sodium lauryl sulphate | 1.88 | 1.88 | 1.88 |
| Triclosan | 0.20 | 0.40 | 0.20 |
| Sodium pyrophosphate | 4.00 | 4.00 | 2.00 |
| Water | to 100.00% | to 100.00% | to 100.00% |

|  | Example 4 % | Example 5 % |
|---|---|---|
| Sorbitol (70% soln) | 22.40 | 30.00 |
| Glycerine | 5.60 | — |
| Saccharin (15% soln) | 2.80 | 2.80 |
| Carboxymethyl cellulose gum | 0.80 | 1.40 |
| Hydroxyethyl cellulose gum | 0.10 | 0.10 |
| Calcium silicate | 0.20 | 0.20 |
| Sodium monofluorophosphate | 0.80 | 0.80 |
| Water | 2.00 | 2.00 |
| Calcium glycerophosphate | 0.13 | 0.13 |
| Calcium carbonate | 45.77 | 33.00 |
| Polyvinyl pyrrolidone | 0.10 | 0.10 |
| Thickening silica | — | 2.00 |
| NaOH (10.2% soln) | — | 1.00 |
| Flavour | 1.15 | 1.15 |
| Sodium lauryl sulphate | 1.88 | 1.88 |
| Sodium carbonate | 0.50 | 0.50 |
| Sodium bicarbonate | 1.50 | 1.50 |
| Triclosan | 0.40 | 0.40 |
| Sodium pyrophosphate | 3.00 | 3.00 |

| Example 6 | % |
|---|---|
| Ethanol | 5.00 |
| Sodium pyrophosphate | 1.80 |
| Sodium Carbonate | 1.00 |
| Flavour | 0.50 |
| Triclosan | 0.05 |
| Water | to 100 |

EXAMPLE 7

Test Data

Effect on plaque growth

The effect of mouthwashes on plaque growth was determined using the method described by Stean H. S. and Forward G. C. (Community Dent. Oral Epidemiol., 1980,8,420–423).

Thirty volunteers cleaned the buccal surfaces of their teeth free of visible plaque using a control dentifrice, after which they rinsed for 1 min. with 10 ml of one of the two test mouthwashes.

After twenty four hours, during which time the volunteers refrained from all forms of oral hygiene, the plaque was disclosed with erythrosin and the area on the buccal surfaces thereby revealed charted by an examiner. The growth of plaque was assessed by measurement of:

(i) the plaque area (Stean H. S. and Forward G. C., Community Dent. Oral Epidemiol., 1980, 8, 420–423)

(ii) the gingival margin plaque index (GMPI) (Harrap C. J., J. Clin. Periodontal., 1974, 1, 166–174).

The mouthwashes were allocated to the subjects in a balanced, randomised fashion and the procedure repeated until each volunteer had used both of the test mouthwashes.

The identity the products was unknown to the volunteers and to the examiner.

The results are presented in the table below:

| Plaque Assessment | Mouthwash[a] plus 0.05% Triclosan | Mouthwash[a] plus 0.05% Triclosan plus 1.8% $Na_4P_2O_7$ | Statistical Significance of Difference[b] |
|---|---|---|---|
| Plaque area | 6.50 | 5.57 | 0.06 |
| GMPI | 15.09 | 13.41 | 0.04 |

[a]Mouthwash consists of Ethanol (5%), Sodium carbonate (1%), flavour (0.50%), and water (to 100%).
[b]Wilcoxon Sign Ranks Test.

The results presented in the table show that the addition of sodium pyrophosphate to a mouthwash containing triclosan significantly reduced the growth of plaque as measured by both plaque area and plaque length, compared to a mouthwash containing triclosan alone. Therefore, the addition of sodium pyrophosphate to such a composition would appear to improve the ability of the composition to reduce dental caries.

We claim:

1. An oral hygiene composition in the form of dentifrice or mouthwash comprising;
   (a) 0.01 to 2% by weight of the composition of an antibacterial compound of formula (I):

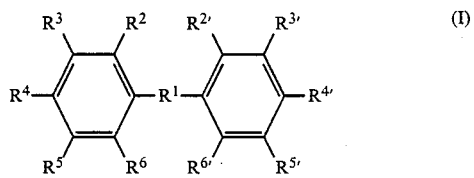

in which $R^1$ is oxygen, sulphur or an alkylene group of from one to six carbon atoms, and each of $R^2$ to $R^6$ and $R^{2'}$ to $R^{6'}$ is hydrogen, hydroxyl or halogen;
   (b) from 0 to 90% by weight of a dentally acceptable abrasive;
   (c) from 0.1 to 15% by weight of a dialkali or a tetraalkali metal pyrophosphate salt, or a mixture thereof, and
   (d) water.

2. A composition according to claim 1 wherein the weight range of component (a) is from 0.01 to 1.0%.

3. A composition according to claim 2 wherein the weight range of component (a) is from 0.05 to 0.5%.

4. A composition according to claim 1 wherein the weight range of component (b) is from 20 to 75%.

5. A composition according to claim 1 wherein the weight range of component (c) is from 2 to 10%.

6. A composition according to claim 1 in which water is present in an amount of from 2 to 95%.

7. A composition according to claim 1 in which the compound of formula (I) is selected from the group consisting of:
5,5'-dichloro-2,2'-dihydroxydiphenyl methane (Dichlorophene);
2,2'-dihydroxy-3,5,6,3',5',6'-hexachloro-diphenylmethane (Hexachlorophene);
3,3'-dibromo-5,5'-dichloro-2,2'-dihydroxydiphenylmethane (Bromochlorophene); and
2,4,4'-trichloro-2'-hydroxydiphenyl ether (Triclosan).

8. A composition according to claim 7 in which the compound of formula (I) is 2,4,4'-trichloro-2'-hydroxydiphenyl ether.

9. A composition according to claim 1 further comprising a water-soluble fluoride-providing compound.

10. A method of reducing or preventing dental plaque in humans which method comprises contacting the tooth surface thereof with an oral hygiene composition according to claim 1.

11. A method of reducing or preventing dental plaque in animals, which method comprises contacting the tooth surface thereof with an oral hygiene composition according to claim 1.

12. A composition according to claim 1 in the form of a dentifrice in which an abrasive is present, wherein the abrasive is selected from the group consisting of calcium carbonate, dicalcium phosphate, calcium pyrophosphate, alumina, silica and synthetic plastics resin particles.

* * * * *